US007687553B2

(12) United States Patent
Beyreuther et al.

(10) Patent No.: US 7,687,553 B2
(45) Date of Patent: *Mar. 30, 2010

(54) METHOD FOR TREATING BONE CANCER PAIN OR CHEMOTHERAPY INDUCED PAIN

(75) Inventors: Bettina Beyreuther, Duesseldorf (DE); Thomas Stohr, Monheim (DE)

(73) Assignee: Schwarz Pharma AG, Monheim (DE)

( * ) Notice: Subject to any disclaimer, the term of this patent is extended or adjusted under 35 U.S.C. 154(b) by 402 days.

This patent is subject to a terminal disclaimer.

(21) Appl. No.: 11/211,476

(22) Filed: Aug. 26, 2005

(65) Prior Publication Data

US 2006/0046957 A1   Mar. 2, 2006

Related U.S. Application Data

(60) Provisional application No. 60/604,810, filed on Aug. 27, 2004.

(30) Foreign Application Priority Data

Aug. 27, 2004  (EP)  ................... 04020402

(51) Int. Cl.
 *A61F 2/28* (2006.01)
 *C12P 13/02* (2006.01)
 *C12P 13/04* (2006.01)
(52) U.S. Cl. .................. 523/115; 435/129; 435/106
(58) Field of Classification Search ................ None
See application file for complete search history.

(56) References Cited

U.S. PATENT DOCUMENTS

| 4,303,673 | A | 12/1981 | Biedermann et al. ......... 424/324 |
|---|---|---|---|
| 4,510,082 | A | 4/1985 | Gesellchen et al. ... 260/112.5 R |
| 4,513,009 | A | 4/1985 | Roques et al. ............... 514/513 |
| 4,533,657 | A | 8/1985 | Morgan ........................ 514/19 |
| 4,618,708 | A | 10/1986 | Roques et al. ............... 562/448 |
| 4,707,468 | A | 11/1987 | Yoshino et al. ............... 514/16 |
| 5,378,729 | A | 1/1995 | Kohn et al. ............... 514/231.2 |
| 5,508,266 | A | 4/1996 | Fink ............................. 514/19 |
| 5,536,853 | A | 7/1996 | Spellmeyer et al. ......... 549/441 |
| 5,656,267 | A | 8/1997 | Sagen et al. ............. 424/93.21 |
| 5,760,038 | A | 6/1998 | Murugesan et al. ......... 514/252 |
| 5,773,455 | A | 6/1998 | Dong et al. .................. 514/365 |
| 5,780,589 | A | 7/1998 | Lazarus et al. ............... 530/331 |
| 5,866,585 | A | 2/1999 | Fogel .......................... 514/289 |
| 5,885,999 | A | 3/1999 | Elliott et al. ................ 514/258 |
| 6,001,876 | A | 12/1999 | Singh .......................... 514/561 |
| 6,028,102 | A | 2/2000 | Bialer et al. ................. 514/489 |
| 6,037,324 | A | 3/2000 | Schwender et al. ........... 514/18 |
| 6,083,941 | A | 7/2000 | Farb ............................ 514/177 |
| 6,083,951 | A | 7/2000 | Bradbury .................... 514/256 |
| 6,103,732 | A | 8/2000 | Amberg et al. .............. 514/269 |
| 6,114,390 | A | 9/2000 | Engel et al. .................. 514/595 |
| 6,126,939 | A | 10/2000 | Eisenbach-Schwartz et al. ......................... 424/185.1 |
| 6,180,611 | B1 | 1/2001 | Montana et al. ............... 514/19 |
| 6,277,825 | B1 | 8/2001 | Olivera et al. ................. 514/13 |
| 6,737,408 | B1 | 5/2004 | Balasubramanium et al. . 514/18 |
| 2003/0216466 | A1 | 11/2003 | Scheuerman et al. ........ 514/513 |
| 2004/0101582 | A1 | 5/2004 | Wolicki |
| 2005/0013856 | A1 | 1/2005 | Trivedi et al. ............... 424/464 |
| 2005/0043675 | A1 | 2/2005 | Pastore et al. ................. 604/67 |
| 2005/0227961 | A1 | 10/2005 | Kucharik et al. ........ 514/211.13 |
| 2005/0261204 | A1 | 11/2005 | Stohr ........................... 514/19 |
| 2005/0277596 | A1 | 12/2005 | Stohr ........................... 514/19 |
| 2005/0288234 | A1 | 12/2005 | Stohr ........................... 514/19 |
| 2006/0009384 | A1 | 1/2006 | Rudd et al. ................... 514/12 |
| 2006/0046957 | A1 | 3/2006 | Beyreuther et al. ............ 514/7 |
| 2006/0135437 | A1 | 6/2006 | Stoehr et al. ................. 514/19 |

FOREIGN PATENT DOCUMENTS

| DE | 195 33 023 | 4/1996 |
|---|---|---|
| EP | 0 555 537 | 8/1993 |
| EP | 0 997 147 | 5/2000 |
| EP | 1 243 263 | 11/2002 |
| EP | 1 486 205 | 12/2004 |
| EP | 1 486 206 | 12/2004 |
| EP | 1 537 862 | 6/2005 |
| EP | 1 541 138 | 6/2005 |
| EP | 1 579 858 | 9/2005 |
| EP | 1 688 137 | 8/2006 |
| WO | WO 92/14706 | 9/1992 |
| WO | WO 95/30645 | 11/1995 |
| WO | WO 96/11209 | 4/1996 |
| WO | WO 96/32100 A1 | 10/1996 |
| WO | WO 97/38980 | 10/1997 |
| WO | WO 97/38981 | 10/1997 |
| WO | WO 98/09953 | 3/1998 |
| WO | WO 99/02146 | 1/1999 |
| WO | WO 99/07413 | 2/1999 |
| WO | WO 99/16444 | 4/1999 |

(Continued)

OTHER PUBLICATIONS

[Retrived from]http://www.answer.com/prevent, 2007, 4 pages [retrieved on Oct. 24, 2007].*
[Retrieved from] http://www.mndaily.com/daily/2000/05/03/news/new5, 2000, 3 pages [retrieved on Feb. 24, 2007].*
[Retrieved from]http://www.cancer.gov/cancertopics/paincontrol/page1/print?page=&keyword=, 2007, 4 pages [retrieved on Oct. 24, 2007].*
Quasthoff, et al., 2002, J. Neurol., 249, 9-17.*
McCleane et al., "Does SPM 927 have an analgesic effect in human neuropathic pain?. . . ", Neuroscience Letters, Dec. 4, 2003, pp. 117-120.
Morrow et al., "Antinociceptive properties of the anticonvulsant SPM927 (Harkoseride) in rat", Society for Neuroscience Abstracts, vol. 27, No. 1, 2001, p. 1332.

(Continued)

*Primary Examiner*—Andrew D Kosar
*Assistant Examiner*—Satyanarayana R Gudibande
(74) *Attorney, Agent, or Firm*—Harness, Dickey & Pierce, P.L.C.

(57) ABSTRACT

The present invention is directed to the use of a class of peptide compounds for treating tumor pain, in particular bone cancer pain, for treating chemotherapy-induced pain and for treating nucleoside-induced pain.

12 Claims, 7 Drawing Sheets

FOREIGN PATENT DOCUMENTS

Figure 1:
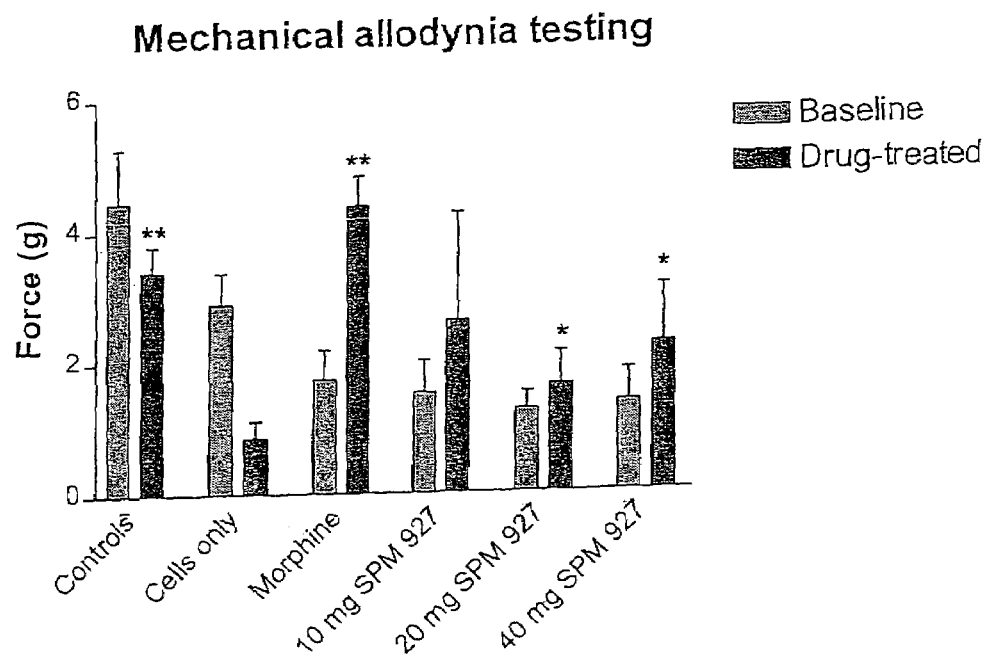

| | | |
|---|---|---|
| WO | WO 99/23078 | 5/1999 |
| WO | WO 99/43309 A2 | 9/1999 |
| WO | WO 00/51586 | 9/2000 |
| WO | WO 01/17976 | 3/2001 |
| WO | WO 01/78762 | 10/2001 |
| WO | WO 02/13766 | 2/2002 |
| WO | WO 02/15922 A2 | 2/2002 |
| WO | WO-02/15922 A2 * | 2/2002 |
| WO | WO 02/42256 | 5/2002 |
| WO | WO 02/074297 A1 | 9/2002 |
| WO | WO 02/074784 | 9/2002 |
| WO | WO 02/076979 | 10/2002 |
| WO | WO 02/087548 | 11/2002 |
| WO | WO 02/088664 | 11/2002 |
| WO | WO 03/000642 | 1/2003 |
| WO | WO 2004/014895 | 2/2004 |
| WO | WO 2004/043926 | 5/2004 |
| WO | WO 2004/046178 | 6/2004 |
| WO | WO 2004/060353 | 7/2004 |
| WO | WO 2004/066987 | 8/2004 |
| WO | WO 2004/066990 | 8/2004 |
| WO | WO 2004/091585 | 10/2004 |
| WO | WO 2004/100871 | 11/2004 |
| WO | WO 2005/053667 A1 | 6/2005 |
| WO | WO 2005/092313 | 10/2005 |
| WO | WO 2005/099740 A1 | 10/2005 |

OTHER PUBLICATIONS

McCleane, "Pharmacological Management of Neuropathic Pain", CNS Drugs 2003, vol. 17, No. 14, 2003, pp. 1031-1043.
Hovinga C A, "SPM-927 Schwarz pharma", IDrugs May 1, 2003, vol. 6, No. 5, May 1, 2003, pp. 479-485.
M. J. O'Neil et al., "The Merck Index, Thirteenth Edition" 2001, Merck Research Laboratories.
Lynch et al., "Attenuation of mechanical allodynia by clinically utilized drugs in a rat chemotherapy-induced neuropathic pain model", Pain, vol. 110, No. 1-2, Jul. 2004, pp. 56-63.
Eckel et al., "Prevention of oxaliplatin-induced neuropathy by carbamazepine: A pilot study", DMW Deutsche Medizinische Wochenschrift, vol. 127, No. 3, Jan. 18, 2002, pp. 78-82.
Nicolaus, "Symbiotic Approach to Drug Design", Decision Making in Drug Research, 1983, pp. 173-186.
Abbott et al. (1995) Pain 60:91-102.
Abdulla & Smith (2002) J. Neurophysiol. 88:2518-2529.
Akiba et al. (2003) Receptors & Channels 9:291-299.
Albensi et al. (2004) Am. J. Alzheimer's Disease & Other Dementias 19:269-274.
Amir et al. (2006) J. Pain 7(5 Suppl. 3):S1-S29.
Arnér & Meyerson (1988) Pain 33:11-23.
Arnt et al. (1984) Pol. J. Pharmacol. Pharm. 36:221-230.
Arroyo (2003) "Safety of SPM 927 in subjects with epilepsy and neuropathic pain" Poster presented at AES Scientific Exhibit, Dec. 5-10, 2003.
Backonja (2002) Neurology 59:S14-S17.
Backonja (2003) Anesth. Analg. 97:785-790.
Béguin et al. (2003) Bioorganic & Medicinal Chemistry 11:4275-4285.
Béguin et al. (2004) Bioorganic & Medicinal Chemistry 12:3079-3096.
Ben-Menachem (2005) "A dose-response, placebo-controlled trial using lacosamide as adjunctive therapy in subjects with partial seizures" Presented at 26th International Epilepsy Congress, Paris, Aug.-Sep. 1, 2005.
Ben-Menachem et al. (2005) "Efficacy and safety of adjunctive oral lacosamide for the treatment of partial-onset seizures in patients with epilepsy" Poster P03.101 presented at American Academy of Neurology 57th Annual Meeting, Miami Beach, FL.
Bennett & Xie (1988) Pain 33(1):87-107 (abstract only www.ncbi.nlm.nih.gov/pubmed12837713).
Bennett et al. (2000) Pain 86:163-175.

Beyak et al. (2004) Am. J. Physiol. Gastrointest. Liver Physiol. 287:G845-G855.
Beyreuther (2004) "Pharmacology of SPM 927 and its relevance to clinical practice for neuropathic pain" Presented at Visiongain Pain Management, 2004.
Beyreuther et al. (2004) "SPM 927 displays potent antinococeptive effects in rat models for inflammatory and neuropathic pain" Poster presented at Neuropathic Pain, May 13-14, 2004.
Beyreuther et al. (2005) "Lacosamide displays antinociceptive effects in a rat model for tumor-induced cancer pain and chemotherapy-induced pain" Poster presented at World Congress on Pain, Aug. 21-26, 2005.
Beyreuther et al. (2005) "Lacosamide displays antinociceptive effects in a rat model for diabetic neuropathic pain" Presented at World Congress on Pain, Aug. 21-26, 2005.
Beyreuther et al. (2006) "Effects of lacosamide as compared to other analgesics: a responder analysis in the streptozotocin rat model for diabetic neuropathic pain" Poster 618 presented at American Pain Society, 2006 (abstract at www.ampainsoc.org/db2/abstract/view?poster_id=2637#618).
Beyreuther et al. (2006) "Lacosamide displays antinociceptive effects in a rat model for musculoskeletal pain induced by TNF" Poster 625 presented at American Pain Society, 2006 (abstract at www.ampainsoc.org/db2/abstract/view?poster_id=2643#625).
Beyreuther et al. (2006) "Lacosamide displays antinociceptive effects in rat models for arthritis pain" Poster 626 presented at American Pain Society, 2006 (abstract at www.ampainsoc.org/db2/abstract/view?poster_id=2644#626).
Beyreuther et al. (2006) Eur. J. Pharmacol. 539:64-70.
Beyreuther et al. (2007) CNS Drug Rev. 13(1)21-42.
Beyreuther et al. (2007) Arthritis Res. Therapy 9:R14, arthritis-research.com/content/9/1/R14.
Bialer et al. (2001) Epilepsy Res. 43:11-58.
Bialer et al. (2002) Epilepsy Res. 51:31-71.
Bilsky et al. (2000) J. Med. Chem. 43:2586-2590.
Biton et al. (2003) Epilepsia 44(Suppl. 9):259, abst. 2.241 (poster attached).
Biton et al. (2004) "Safety and tolerability of lacosamide solution for infusion" Poster presented at AES Scientific Exhibit, Dec. 3-7, 2004.
Biton et al. (2005) "Safety and tolerability of intravenous lacosamide as replacement for oral lacosamide in subjects with partial seizures" Poster P02.148 presented at International Epilepsy Congress, Aug. 28-Sep. 1, 2005.
Biton (2006) "Multicenter, double-blind, double-dummy trial investigating safety, tolerability and pharmacokinetics of intravenous lacosamide (SPM 927) in subjects with partial seizures" Presented at European Congress on Epileptology 2006.
Blackburn-Munro et al. (2002) Eur. J. Pharmacol. 445:231-238.
Blair & Bean (2002) J. Neurosci. 22(23):10277-10290.
Blair & Bean (2003) J. Neurosci. 23(32):10338-10350.
Bretschneider et al. (2006) www.ampainsoc.org/db2/abstract/view?poster_id=2765#766.
Brodie (1996) Can. J. Neurol. Sci. 23(Suppl. 2):S6-S9.
Bunney & Garland (1982) Pharmacopsychiat. 15:111-115.
Caliendo et al. (2005) Curr Med. Chem. 12(15):1721-1753.
Calvino et al. (1987) Behavioural Brain Res. 24:11-29.
Casey et al. (2003) Neuropsychopharmacol. 28:182-192.
Cawello et al. (2003) Epilepsia 44(Suppl. 9):95, abst. 1.265 (poster attached).
Cawello et al. (2004) Epilepsia 45(Suppl. 7):307, abst. 2.342 (poster attached).
Chen & Lipton (2006) J. Neurochem. 97:1611-1626.
Chevrier et al. (2004) Br. J. Pharmacol. 142:576-584.
Christensen et al. (1996) Pain 68:97-107.
Citrome (2003) Psychopharmacol. Bull. 37(Suppl. 2):74-88.
Colpaert et al. (1982) Life Sciences 31:67-75.
Cummins et al. (2004) J. Neurosci. 24(38):8232-8236.
Daniels et al. (2005) "Long-term safety and efficacy of lacosamide as adjunctive therapy in subjects with partial seizures: 96-week follow-up" Poster presented at AES Scientific Exhibit, Dec. 2-5, 2005.
Decosterd & Woolf (2000) Pain 87:149-158.
Doty et al. (2004) in Bialer et al., Epilepsy Res. 61:1-48, pp. 14-16.

Doty et al. (2004) "Update on the clinical development of SPM 927 (formerly harkoseride)" Presented at EILAT VII, May 2004.
Dowdall et al. (2005) Pharmacol. Biochem. Behavior 80:93-108.
Dubuisson & Dennis (1977) Pain 4:161-174.
Duncan & Kohn (2005) Epilepsy Res. 67:81-87.
Eller et al. (2005) Neurosurg. Focus 18(5):E3, 3 pp.
Elliott (1997) Brain Res. 754:221-226.
Erichsen & Blackburn-Munro (2002) Pain 98:151-161.
Errington et al. (2005) "Lacosamide has a unique molecular mode of action" Poster presented at AES Scientific Exhibit, Dec. 2-5, 2005.
Everill et al. (2001) Neurosci. 106(1):161-169.
Field et al. (1997) Br. J. Pharmacol. 121:1513-1522.
Field et al. (2002) J. Pharmacol. Exp. Ther. 303(2):730-735.
Fountain et al. (2000) Epilepsia 41(Suppl. 7):169 (presentation attached).
Freynhagen et al. (2005) Pain 115:254-263.
Grippo et al. (2005) Psychopharmacol. 179:769-780.
Hama et al. (1999) Pharmacol. Biochem. Behavior 62:67-74.
Han et al. (2000) Pain 84:253-261.
Hao et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.
Heers et al. (2006) "The preclinical profile of the novel anticonvulsant lacosamide" Poster presented at European Congress on Epileptology 2006.
Henriksson (1999) Baillière's Clin. Rheumatol. 13(3):455-461.
Hidvegi et al. (2006) "Lacosamide in subjects with painful distal diabetic neuropathy: results of a multi-center, open-label, follow-on trial" Poster presented at American Pain Society, May 3-6, 2006.
Hofmann et al. (2003) Eur. J. Pharmacol. 470:17-25.
Holmberg et al. (2004) J. Med. Chem. 47:3927-3930.
Hong et al. (2004) J. Biol. Chem. 279(28):29341-29350.
Honore et al. (2000) Neurosci. 98(3):585-598.
Horstmann et al. (2002) Epilepsia 43(Suppl. 7):188, abst. 2.174 (poster attached).
Horstmann et al. (2003) Epilepsia 44(Suppl. 9):97, Abst. 1.271 (poster attached).
Horstmann et al. (2003) "SPM 927 does not prolong the QTc interval" Poster presented at 6th International Conference on the Mechanisms and Treatment of Neuropathic Pain, San Francisco, Sep. 18-20, 2003.
Hunskaar et al. (1985) J. Neurosci. Methods 14:69-76.
Hunt (2003) Clin. Orthopaedics Rel. Res. 409:96-105.
Hurley et al. (2002) Anesthesiology 97:1263-1273.
Ilyin et al. (2005) Br. J. Pharmacol. 144:801-812.
Jain (2000) Emerging Drugs 5(2):241-257.
Jensen (2000) Eur. J. Neurol. 7(Suppl. 3):3-4, abst. MT-9.
Kalso (2005) Curr. Pharm. Design 11:3005-3011.
Kemp & McKernan (2002) Nature Neurosci. Suppl. 5:1039-1042.
Kenney et al. (2006) www.ampainsoc.org/db2/abstract/view?poster_id=2773#774.
Kim & Chung (1992) Pain 50(3):355-363.
Kohn et al. (1991) J. Med. Chem. 34:2444-2452.
Kropeit et al. (2004) Epilepsia 45(Suppl. 7): 123, abst. 1.323 (poster attached).
Kropeit et al. (2005) "Low drug-interaction potential of Lacosamide" Poster 702 presented at American Pain Society 2005 (abstract at www.ampainsoc.org/db2/abstract/view?poster_id=2394#702).
Kropeit et al. (2006) "Lacosamide has low potential for drug-drug-interaction" Poster 851 presented at American Pain Society 2006 (abstract at www.ampainsoc.org/db2/abstract/view?poster_id=2848 #851).
Lai et al. (2003) Curr. Opin. Neurobiol. 13:291-297.
Lai et al. (2004) Ann. Rev. Pharmacol. Toxicol. 44:371-397.
Lampert et al. (2006) Exp. Brain Res. 174(4):660-666.
Lawand et al. (1997) Eur. J. Pharmacol. 324:169-177.
Lee et al. (2000) NeuroReport 11(4):657-661.
Lee & Jeong (2002) J. Korean Med. Sci. 17:81-85.
Lesser et al. (2004) Neurology 63:2104-2110.
LeTiran et al. (2002) J. Med. Chem. 45:4762-4773.
Lockwood et al. (2002) N. Engl. J. Med. 347(12):904-910.
Lu & Westlund (1999) J. Pharmacol. Exp. Ther. 290:214-219.

Mach et al. (2002) Neurosci. 113(1):155-166.
Macres (2000) "Understanding neuropathic pain" www.spineuniverse.com/displayarticle.php/article1614.html.
Maier et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.
Majumdar et al. (2004) Eur. J. Neurosci. 20:127-143.
March (1985) Advanced Organic Chemistry, New York: Wiley, pp. 16-18.
Meinardi (1995) in Levy et al., ed. "Antiepileptic Drugs", 4th ed., chap. 6, pp. 91-97; New York: Raven Press.
Mohapatra et al. (2003) Mol. Cell. Neurosci. 23:314-324.
Moller (2000) J. Am. Acad. Audiol. 11(3):115-124.
Morrow et al. (2003) "The effects of lacosamide in animal models for acute, inflammatory and neuropathic pain" Poster presented at AES Scientific Exhibit, Dec. 5-10, 2003.
Nakata et al. (2003) Biol. Psychiatry 53:571-576.
Papapetropoulos & Singer (2007) Seminars in Neurology 27(2):183-194.
Patel et al. (2001) Pain 90:217-226.
Pessoa-Mahana et al. (2003) Mini Rev. Med. Chem. 3:77-93.
Priestley (2004) Curr. Drug Targets—CNS & Neurol. Disorders 3:441-456.
Randall & Selitto (1957) Arch. Int. Pharmacodyn. 91:409-419.
Rauck et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.
Rauck et al. (2007) Clin. J. Pain 23(2):150-158.
Rauschkolb et al. (2004) "SPM 927, a novel promising pain treatment" Presented at Visiongain Pain Management, 2004.
Remy et al. (2004) Neuropharmacol. 47:1102-1112.
Richeimer (2000) "The Richeimer Pain Update" www.helpforpain.com/arch2000dec.htm.
Rodger (1991) Can. Med. Assoc. J. 145:1571-1581.
Rosenfeld et al. (2003) Epilepsia 44(Suppl. 9):262, abst. 2.249 (poster attached).
Rosenfeld et al. (2005) Epilepsia 46(Suppl. 8):184, abst. 2.278 (poster attached).
Rosenstock et al. (2004) Pain 110:628-638.
Rüttiger et al. (2003) Hear. Res. 180:39-50.
Sachdeo et al. (2003) "An open-label, maximum tolerated dose trial to evaluate oral SPM 927 as adjunctive therapy in patients with partial seizures" Poster presented at 55th Annual Meeting, American Academy of Neurology, Mar. 2003.
Saddi & Abbott (2000) Pain 89:53-63.
Schiltmeyer et al. (2004) Epilepsia 45(Suppl. 7):313, abst. 2.361 (poster attached).
Schiltmeyer et al. (2006) "No interaction between lacosamide and metformin" Poster 850 presented at American Pain Society 2006 (abstract at www.ampainsoc.org/db2/abstract/view?poster_id=2847 #850).
Seltzer et al. (2001) Pain 93:101-106.
Shaibani at al. (2005) "An open-label follow-on trial to assess the long-term safety and efficacy of oral lacosamide in subjects with diabetic neuropathy" Poster presented at World Congress on Pain, Aug. 21-26, 2005.
Shiro et al. (1996) Psychiatry Clin. Neurosci. 50:141-146.
Silver & Soderlund (2005) Neurotoxicol. 26:397-406.
Sindrup & Jensen (1999) Pain 83:389-400.
Sommerville (2003) "Schwarz Pharma's Neurology Pipeline" www.schwarzpharma.com/_uploads/assets/1369_4_neurology_KNS_190203.pdf.
Sommerville & Whitesides (2004) "Intravenous SPM 927 (formerly harkoseride)" Presented at EILAT VII, May 2004.
Stein et al. (1988) Pharmacol. Biochem. Behavior 31:445-451.
Stoehr et al. (2005) "Lacosamide displays potent antinociceptive effects in animal models for neuropathic and inflammatory pain" Poster presented at World Congress on Pain, Aug. 21-26, 2005.
Stoehr & Beyreuther (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.
Stoehr et al. (2006) Eur. J. Pain 10:241-249.
Teng & Abbott (1998) Pain 76:337-347.
Tjølsen (1992) Pain 51:5-17.
Tjølsen & Hole (1997) in Dickinson & Besson, ed., "The Pharmacology of Pain", chap. 1, pp. 1-20; Berlin: Springer-Verlag.
Vaiciene et al. (2006) "Multicenter, open-label trial investigating safety and tolerability of intravenous lacosamide (SPM 927) as replacement for oral lacosamide in subjects with partial seizures: report of first cohort" Poster presented at European Congress on Epileptology 2006.
Vos et al. (1994) J. Neurosci. 14(5):2708-2723.
Watson et al. (1997) Pain 70:53-58.
Wheeler-Aceto et al. (1990) Pain 40:229-238.
Wheeler-Aceto & Cowan (1991) Psychopharmacol. 104:35-44.
Whitesides et al. (2004) "Long-term safety and efficacy of lacosamide as adjunctive therapy in subjects with partial seizures: 48-week follow-up" Poster presented at AES Scientific Exhibit, Dec. 3-7, 2004.
Wood et al. (2002) in "Sodium Channels and Neuronal Hyperexcitability", pp. 159-172; Chichester: Wiley.
Wood et al. (2004) J. Neurobiol. 61:55-71.
Wu et al. (2005) J. Physiol. 565.2:371-380.
Wymer et al. (2005) "A multi-center, randomized double-blind, placebo-controlled trial to assess the efficacy and safety of lacosamide in subjects with painful distal diabetic neuropathy." 8th Int. Conf. on Mechanisms and Treatment of Neuropathic Pain, San Francisco, Nov. 3-5, 2005.
Xu et al. (1992) Pain 48(2):279-290 (abstract only).
Yezierski et al. (1998) Pain 75:141-155.
Ziegler et al. (2005) "Efficacy and safety of lacosamide in the treatment of neuropathic pain attributed to distal diabetic neuropathy." 8th Int. Conf. on Mechanisms and Treatment of Neuropathic Pain, San Francisco, Nov. 3-5, 2005.

* cited by examiner

Figure 4: Cold bath (thermal allodynia)

* $p < 0.05$, Dunnett's test vs vincristine/vehicle

Figure 5: Hot plate 38°C (thermal allodynia)
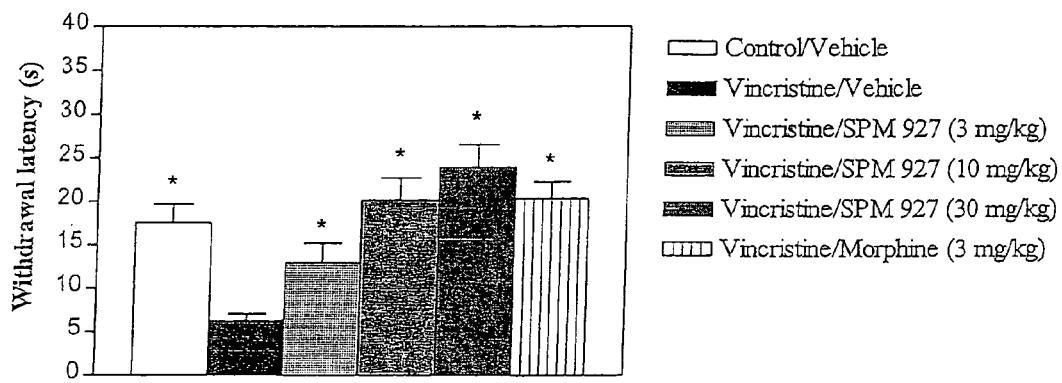
* $p < 0.05$, Dunnett's test vs vincristine/vehicle
Figure 6: Hot plate 52°C (thermal hyperalgesia)
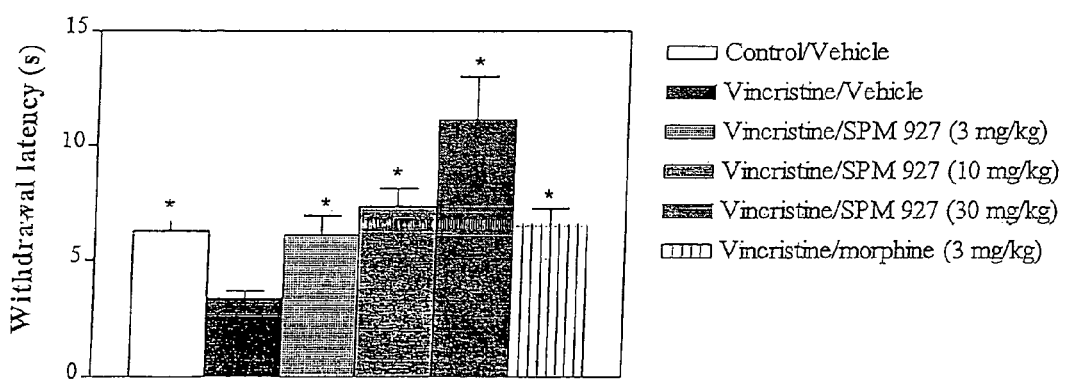
* $p < 0.05$, Dunnett's test vs vincristine/vehicle Figure 7: Paw pressure test (mechanical hyperalgesia)
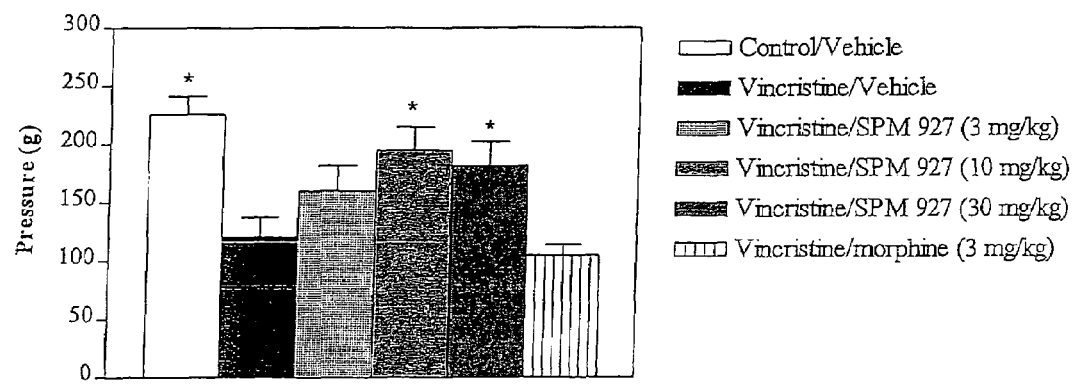
* p < 0.05, Dunnett's test vs vincristine/vehicle
Figure 8: Von Frey hair stimulation test (mechanical allodynia)
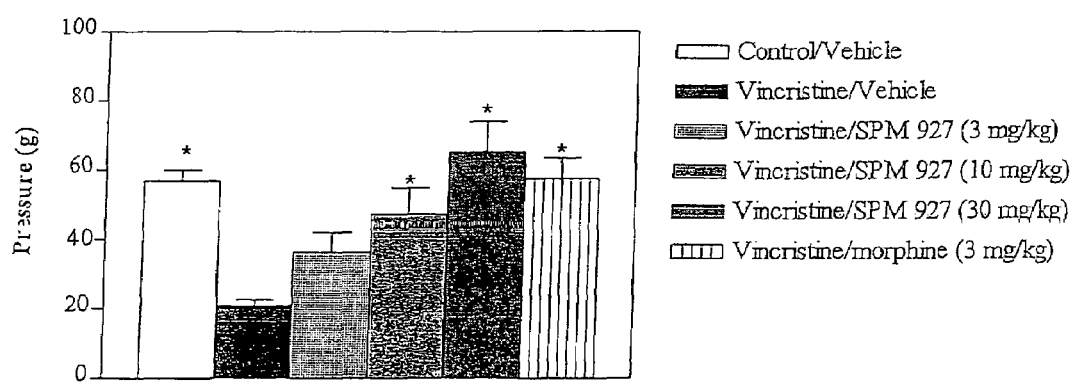
* p < 0.05, Dunnett's test vs vincristine/vehicle Figure 9: Cold bath (thermal allodynia)
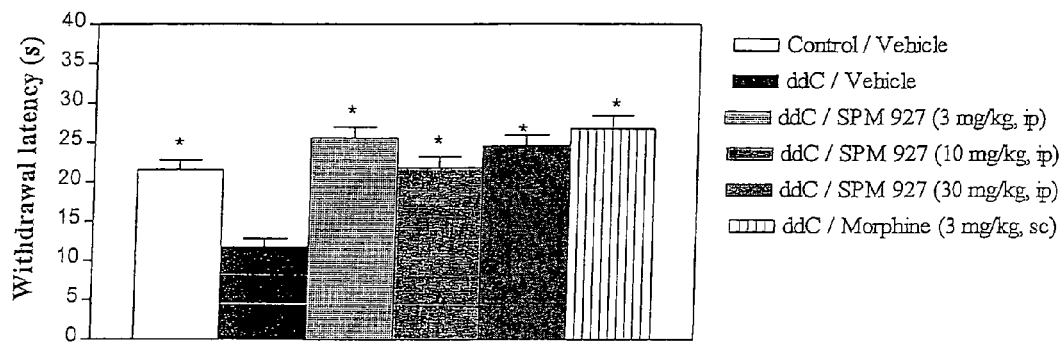
* $p < 0.05$, Dunnett's test vs ddC/vehicle
Figure 10: Brushing test (mechanical allodynia) D20
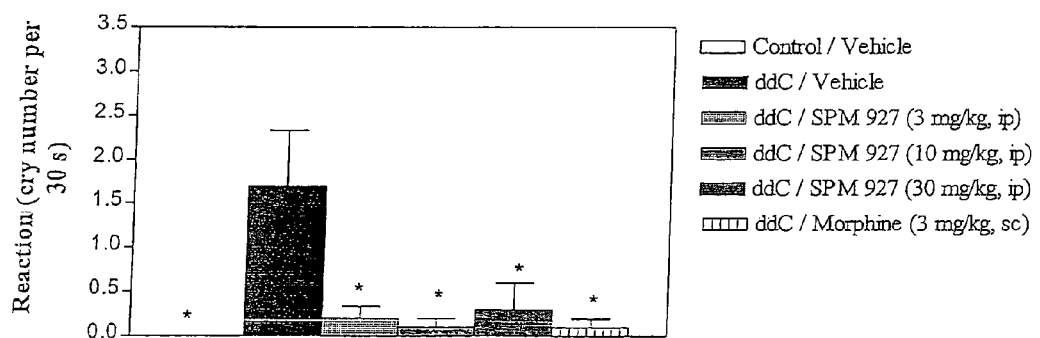
* $p < 0.05$, Dunnett's test vs ddC/vehicle Figure 11: Von Frey Filament test (mechanical allodynia)
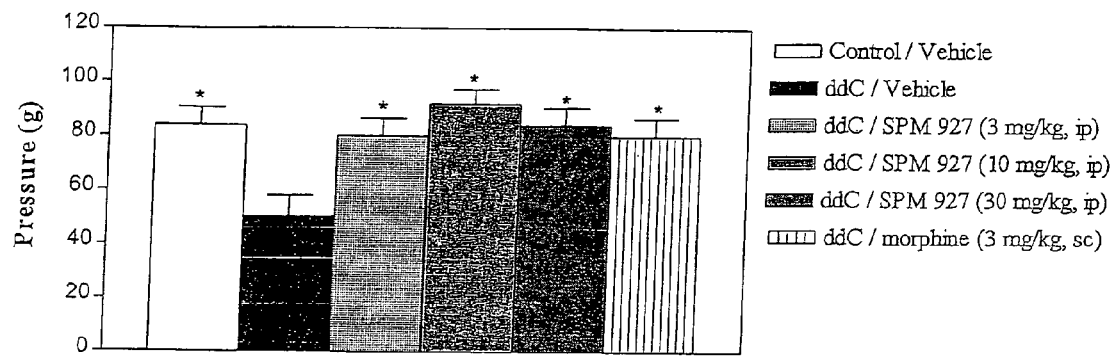
* p < 0.05, Dunnett's test vs ddC/vehicle
Figure 12: Hot plate test 52°C (thermal hyperalgesia)
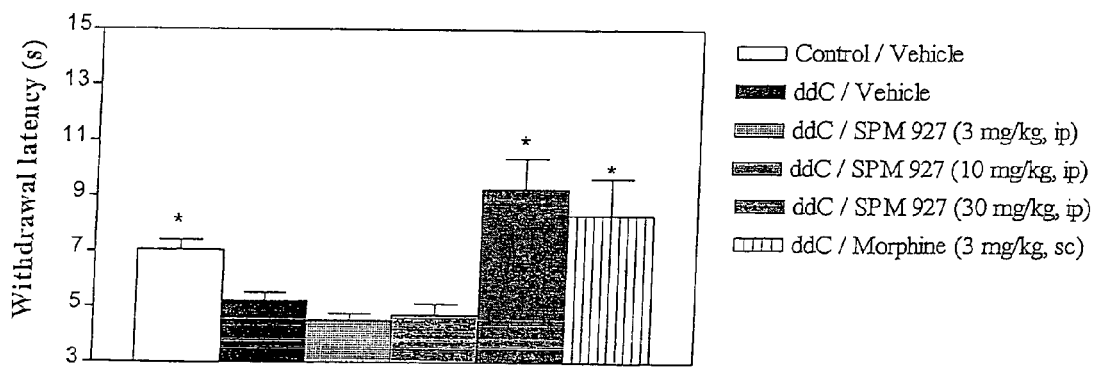
* p < 0.05, Dunnett's test vs ddC/vehicle Figure 13: Paw pressure test (mechanical hyperalgesia)
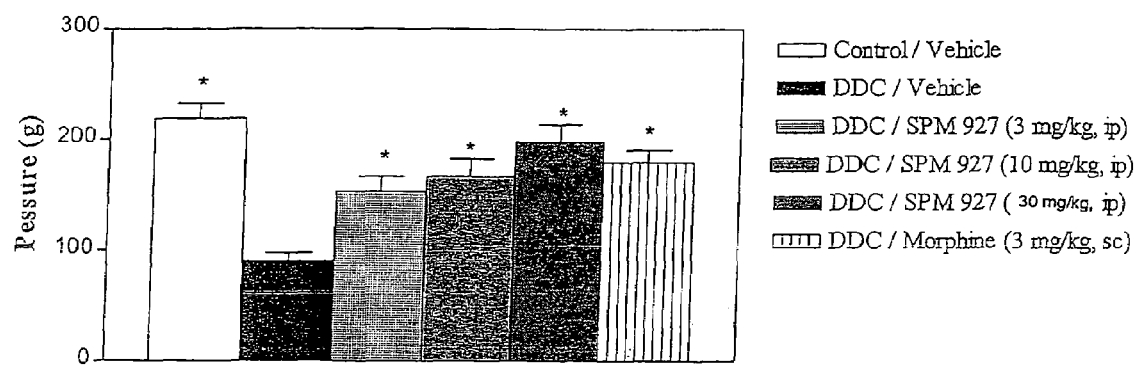
* $p < 0.05$, Dunnett's test vs ddC/vehicle

METHOD FOR TREATING BONE CANCER PAIN OR CHEMOTHERAPY INDUCED PAIN

CROSS REFERENCE TO RELATED APPLICATION

This application claims the benefit of U.S. Provisional 60/604,810, filed Aug. 27, 2004.

The present invention is directed to the use of a class of peptide compounds for treating tumor pain, in particular bone cancer pain, for treating chemotherapy-induced pain and for treating nucleoside-induced pain.

Certain peptides are known to exhibit central nervous system (CNS) activity and are useful in the treatment of epilepsy and other CNS disorders. These peptides which are described in the U.S. Pat. No. 5,378,729 have the Formula (Ia):

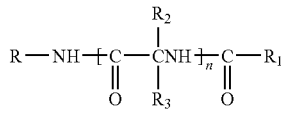

Formula (Ia)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR$, $ONR_4R_7$, $OPR_4R_5$, $PR_{40}R_5$, $SNR_4R_7$, $NR_4SR_7$, $SPR_4R_5$ or $PR_4SR_7$, $NR_4PR_5R_6$ or $PR_4NR_5R_7$,

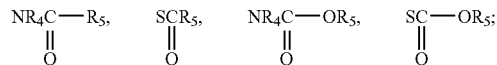

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and $R_7$ is $R_6$ or $COOR_8$ or $COR_8$;

$R_8$ is hydrogen or lower alkyl, or aryl lower alkyl, and the aryl or alkyl group may be unsubstituted or substituted with an electron withdrawing group or an electron donating group; and n is 1-4; and a is 1-3.

U.S. Pat. No. 5,773,475 also discloses additional compounds useful for treating CNS disorders. These compounds are N-benzyl-2-amino-3-methoxy-propionamide having the Formula (IIa):

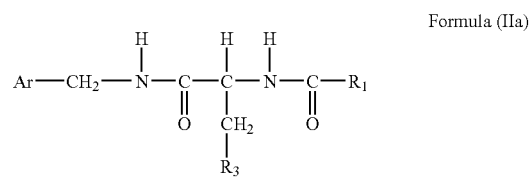

Formula (IIa)

wherein

Ar is aryl which is unsubstituted or substituted with halo; $R_3$ is lower alkoxy; and $R_1$ is methyl.

The patents U.S. Pat. No. 5,378,729 and U.S. Pat. No. 5,773,475 are hereby incorporated by reference. However, neither of these patents describes the use of these compounds for treating tumor pain, in particular bone cancer pain, for treating chemotherapy-induced pain and for treating nucleoside-induced pain.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) or/and Formula (IIa) showing antinociceptive properties for treating different types and symptoms of acute and chronic pain, especially non neuropathic inflammatory pain, e.g. rheumatoid arthritic pain or/and secondary inflammatory osteo-arthritic pain.

At present no analgesic exists which is highly potent in various pain syndromes. Different mechanisms leading to inflammatory or neuropathic pain make it difficult to identify compounds which have general analgesic activity. We are only at the beginning of understanding the mechnisms behind different pain syndromes like cancer pain (e.g. tumor-induced bone cancer pain), chemotherapy-induced pain or nucleoside-induced pain which seem all to have various molecular origins. Antidepressents, anticonvulsants or opioids which describe groups of compounds used in pain treatment do not have a common pattern regarding their efficacy in treatment of pain syndromes. This makes it difficult to predict the activity of new compounds in the various pain syndromes and demands a detailed characterization in multiple pain animal models.

Neuropathic pain after injury or dysfunction to the peripheral or central nervous system remains a difficult clinical problem for which effective treatments are lacking (Bennett, 1994; Murphy and Reid, 2001). Anticonvulsants are used for the management of some forms of neuropathic pain (Sindrup and Jenssen, 1999; Jensen, 2002). SPM 927 (R-2-acetamido-N-benzyl-3-methoxypropionamide) also called harkoseride or ADD 234037 is a novel anticonvulsant drug. It belongs to a series of functionalized amino acids which have been synthesised as a new class of anti-convulsant agents (Kohn et al. 1991).

The present studies show analgesic effects of SPM 927 in rat models of cancer pain, in particular bone cancer pain, of chemotherapy-induced pain and of nucleoside analogue-induced pain.

Bone is the third most common site of metastasis after lung and liver, and is the primary site of metastatic disease in patients with breast, prostate and lung cancer. The bone lesions that result from metastatic disease also cause severe bone pain, which is a major clinical problem in cancer patients. This type of pain is difficult to treat due to its intermittent, progressive nature, and its aggravation by movement. The predominant symptom in this model of pain is mechanical allodynia. Thermal hyperalgesia and mechanical hyperalgesia has also been demonstrated as measured by the weight bearing difference in the two hindlimbs (Medhurst et al., 2002). Treatment of bone pain in human patients is largely limited to the use of opioids, however the efficacy of potent opioids is minimal, and effective doses produce a range of debilitating side effects. Consequently, there is a clinical need for new therapies that can be used to prevent, treat and alleviate tumor-induced bone pain. Candidate therapies for treatment of tumor-induced bone pain can be evaluated using a rat model as the rat is superior for testing behavioral responses to pain stimuli. One model involves the injection of rat mammary gland carcinoma cells into the marrow space of the proximal tibia using an endpoint of pain assessment (Medhurst et al., 2002), which was performed on Days 7 to 15 following tumor implantation.

Chemotherapy-induced pain is a form of neuropathic pain associated with neurotoxic drugs such as vinca alkaloids, e.g. vincristine and is characterized by painful paresthesias and dysesthesias. The clinical antineoplastic efficacy of vincristine is limited by the development of a mixed sensorimotor neuropathy (Casey et al., 1973, Tanner et al., 1998 et al. 1998) that appears to occur in two major stages (Weiss et al., 1974). In the early stage, peripheral axons are damaged by vincristine and the principal symptoms are paresthesias and dysesthesias. In the later stage, which occurs more frequently when higher doses are given for longer periods of time, axons are lost and the principal clinical finding is loss of motor function. The described vincristine rat model seems to reflect the early stage of vincristine-induced chemotherapeutic neuropathy. Whilst the underlying mechanism is not fully understood as yet, it has been described to cause a disorganization of the axonal microtubule cytoskeleton, as well as an increase in the caliber of unmyelinated sensory axons (Quasthoff et al., 2002). These results demonstrated that changes in microtubule structure in nociceptive sensory neurons accompany vincristine-induced hyperalgesia.

Painful peripheral neuropathy, induced by nucleoside analogues is becoming recognized as an important source of morbidity in human immunodeficiency virus (HIV) infected individuals (Cohen, 2002). This severely debilitating side-effect may force abbreviation or even discontinuation of AIDS (acquired immunodeficiency syndrome) therapy (Yatvin et al., 1999). This neuropathy is characterized by a sudden onset of intense burning discomfort in both feet sparing the hands at about the 10th week of treatment, which reached severe intensity over a period of days (Dubinsky et al., 1989). The biochemical mechanism underlying this neuropathic remains to be clearly established, although mitochondrial toxicity has been reported to contribute to the development of this neuropathy. Recently, it has been reported that intoxication of rats with anti-retroviral nucleoside analogue AIDS therapy drugs (ddC (2',3'-dideoxycytidine), ddI (2',3'-dideoxyinosine) or d4T (2',3'-didehydro-3'-deoxythymidine)), produces enhanced nociception in the rat (Joseph et al., 2004). The mechanism involved appears different from that found to contribute in other models of metabolic or toxic painful peripheral neuropathy, as anti-hyperalgesic drugs effective in these models. Inhibitors of protein kinase A, protein kinase C, protein kinase G, p42/p44-mitogen-activated protein kinase (ERK1/2) and nitric oxide synthase have no effect on peripheral neuropathies, and had no effect on nucleoside reverse transcriptase inhibitor-induced hypersensitivity. Intracellular calcium modulators (TMB-8 and Quin-2) are the only agents capable of reversing this hypersentivity of intoxicated animals strongly suggests the role of intracellular calcium in this type of neuropathic pain.

Chemotherapy, e.g. treatment with vinca alkaloids like vincristine or with taxol, suramin, cisplatin, carboplatin or oxaliplatin is used for the treatment of cancer and HIV patients. Additionally, HIV or/and tumor patients are also treated with antiretrovirals or antivirals.

The use of compounds of Formula (Ib) or/and Formula (IIb) for treatment of tumor pain, in particular bone cancer pain, for treating chemotherapy-induced pain and for treating nucleoside-induced pain, has not been reported. Thus, the present invention concerns the use of said compounds of Formulae (Ib) or/and (IIb) for the preparation of a pharmaceutical composition for the prevention, alleviation or/and treatment of tumor pain, in particular tumor pain associated withs AIDS, bone cancer pain, pain produced during tumor progression by infiltration in or pressure on bone, viscera, soft tissue or nerves or/and metastasis-induced pain such as, but not limited to, metastasis-induced bone cancer pain, pain induced by metastatic disease in patients with breast, prostate or lung cancer. The present invention further concerns the use of the compounds of Formula (Ib) or/and (IIb) for the preparation of a pharmaceutical composition for the prevention, alleviation or/and treatment of chemotherapy-induced pain, such as, but not limited to, chemotherapy-induced neuropathic pain, vinca alkaloid-induced pain, vincristine-induced pain or/and pain induced by taxol, suramin, cisplatin, carboplatin or/and oxaliplatin. The present invention further concerns the use of the compounds of Formula (Ib) or/and (IIb) for the preparation of a pharmaceutical composition for the prevention, alleviation or/and treatment of nucleoside- or/and nucleoside analogue-induced pain, such as, but not limited to, painful peripheral neuropathy induced by nucleosides or/and nucleoside analogues, pain induced by anti-tumor or/and anti-viral nucleoside analogues or/and pain induced by anti-retroviral nucleoside analogues, such as AZT (3'-azidothymidine), ddC, ddI or/and d4T, e.g. in AIDS therapy.

The invention also concerns the use of the compounds of Formula (Ib) or/and (IIb) for the preparation of a pharmaceutical composition for the prevention, alleviation or/and treatment of tumor pain, chemotherapy-induced pain, or/and pain induced by at least one nucleoside or/and at least one nucleoside analogue.

Surprisingly, the application of compounds (Ib) or/and (IIb), particularly (R)-2-acetamide-N-benzyl-3-methoxypropionamide (SPM 927) reduced mechanical and thermal hyperalgesia as well as mechanical and thermal allodynia in a tumor-induced bone cancer pain model, in a chemotherapy-induced and a nucleoside analogue-induced neuropathic pain model.

A compound according to the invention has the general Formula (Ib)

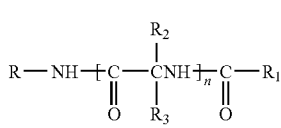

Formula (Ib)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, and/or at least one electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with at least one electron donating group and/or at least one electron withdrawing group;

and $R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group and/or at least one electron donating group;

Z is O, S, $S(O)_a$, $NR_4$, $NR'_6$, $PR_4$ or a chemical bond;

Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with at least one electron donating group and/or at least one electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $N'R_5R_6R_7$,

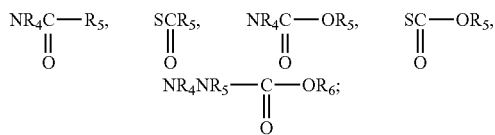

$R'_6$ is hydrogen, lower alkyl, lower alkenyl, or lower alkenyl which may be unsubstituted or substituted with at least one electron withdrawing group or/and at least one electron donating group;

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with at least one electron withdrawing group or/and at least one electron donating group;

$R_7$ is $R_6$ or $COOR_8$ or $COR_8$, which $R_7$ may be unsubstituted or substituted with at least one electron withdrawing group or/and at least one electron donating group;

$R_8$ is hydrogen or lower alkyl, or aryl lower alkyl, and the aryl or alkyl group may be unsubstituted or substituted with at least one electron withdrawing group or/and at least one electron donating group; and n is 1-4; and a is 1-3.

Preferably the compound according has the general Formula (IIb)

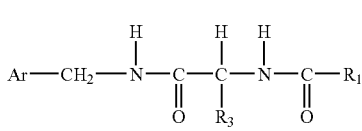

Formula (IIb)

wherein

Ar is aryl, especially phenyl, which is unsubstituted or substituted with at least one halo; $R_3$ is —$CH_2$-Q, wherein Q is lower alkoxy; and $R_1$ is lower alkyl, especially methyl.

The present invention is also directed to a pharmaceutical composition comprising a compound according to Formula (Ib) or/and Formula (IIb) useful for the prevention, alleviation or/and treatment of tumor pain, in particular tumor pain associated with AIDS, bone cancer pain, pain produced during tumor progression by infiltration in or pressure on bone, viscera, soft tissue or nerves or/and metastasis-induced pain such as, but not limited to, metastasis-induced bone cancer pain, pain induced by metastatic disease in patients with breast, prostate or lung cancer. The present invention further concerns a pharmaceutical composition comprising a compound according to Formula (Ib) or/and Formula (IIb) useful for the prevention, alleviation or/and treatment of chemotherapy-induced pain, such as, but not limited to, chemotherapy-induced neuropathic pain, vinca alkaloid-induced pain, vincristine-induced pain or/and pain induced by taxol, suramin, cisplatin, carboplatin or/and oxaliplatin. The present invention further concerns a pharmaceutical composition comprising a compound according to Formula (Ib) or/and Formula (IIb) useful for the prevention, alleviation or/and treatment of nucleoside- or/and nucleoside analogue-induced pain, such as, but not limited to, painful peripheral neuropathy induced by nucleosides or/and nucleoside analogues, pain induced by anti-tumor or/and anti-viral nucleoside analogues or/and pain induced by anti-retroviral nucleoside analogues, such as AZT, ddC, ddI or/and d4T, e.g. in AIDS therapy.

The invention also concerns a pharmaceutical composition comprising a compound according to Formula (Ib) or/and Formula (IIb) useful for the prevention, alleviation or/and treatment of tumor pain, chemotherapy-induced pain, or/and pain induced by at least one nucleoside or/and at least one nucleoside analogue.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenylethyl, phenylpropyl, phenylisopropyl, phenylbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl. Aryl groups may be unsubstituted or mono or polysubstituted with electron withdrawing or/and electron donating groups as described below.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1,3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, haloalkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched.

These groups include, for example, formyl, acetyl, propionyl, butyryl, isobutyryl, tertiary butyryl, pentanoyl and hexanoyl.

As employed herein, a heterocyclic group contains at least one sulfur, nitrogen or oxygen ring atom, but also may include several of said atoms in the ring. The heterocyclic groups contemplated by the present invention include heteroaromatics and saturated and partially saturated heterocyclic compounds. These heterocyclics may be monocyclic, bicyclic, tricyclic or polycyclic and are fused rings. They may preferably contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or polysubstituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl especially those wherein the phenyl ring thereof is unsubstituted or substituted with electron donating groups or/and electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl) amino, amino lower alkyl, mercapto, mercaptoalkyl, alkylthio, and alkyldithio. The term "sulfide" encompasses mercapto, mercapto alkyl and alkylthio, while the term disulfide encompasses alkyidithio. Especially preferred electron donating or/and electron withdrawing groups are halo or lower alkoxy, most preferred are fluoro or methoxy. These preferred substituents may be present on any one of the groups in Formula (Ib) or/and (IIb), e.g. R, $R_1$, $R_2$, $R_3$, $P_4$, $R_5$, $R_6$, $R'_6$, $R_7$, $R_8$ and/or $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl], and o-hydroxylamino (—O—NH$_2$); alkylamido such as acetamido; trifluoroacetamido; lower alkoxyamino, (e.g., NH(OCH$_3$); and heterocyclicamino, such as pyrazoylamino.

The preferred heterocyclic groups representative of R$_2$ and R$_3$ are monocyclic 5- or 6-membered heterocyclic moieties of the formula:

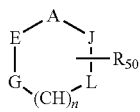

or those corresponding partially or fully saturated form thereof wherein n is 0 or 1; and R$_{50}$ is H or an electron withdrawing group or electron donating group;

A, E, L, J and G are independently CH, or a heteroatom selected from the group consisting of N, O, S;

but when n is O, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When R$_2$ or R$_3$ is a heterocyclic of the above formula, it may be bonded to the main chain by a ring carbon atom. When n is 0, R$_2$ or R$_3$ may additionally be bonded to the main chain by a nitrogen ring atom.

Other preferred moieties of R$_2$ and R$_3$ are hydrogen, aryl, e.g., phenyl, aryl alkyl, e.g., benzyl and alkyl.

It is to be understood that the preferred groups of R$_2$ and R$_3$ may be unsubstituted or mono or poly substituted with electron donating or/and electron withdrawing groups. It is preferred that R$_2$ and R$_3$ are independently hydrogen, lower alkyl, which is either unsubstituted or substituted with electron withdrawing groups or/and electron donating groups, such as lower alkoxy (e.g., methoxy, ethoxy, and the like), N-hydroxylamino, N-lower alkylhydroxyamino, N-loweralkyl-O-loweralkyl and alkylhydroxyamino.

It is preferred that one of R$_2$ and R$_3$ is hydrogen.

It is preferred that n is one.

It is more prefered that n=1 and one of R$_2$ and R$_3$ is hydrogen. It is especially preferred that in this embodiment, R$_2$ is hydrogen and R$_3$ is lower alkyl or ZY; Z is O, NR$_4$ or PR$_4$; Y is hydrogen or lower alkyl; ZY is NR$_4$NR$_5$R$_7$, NR$_4$OR$_5$,

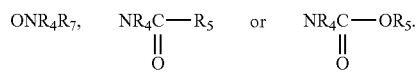

In another especially preferred embodiment, n=1, R$_2$ is hydrogen and R$_3$ is lower alkyl which may be substituted or unsubstituted with an electron donating or electron withdrawing group, NR$_{40}$R$_5$, or ONR$_4$R$_7$, In yet another especially preferred embodiment, n=1, R$_2$ is hydrogen and R$_3$ is lower alkyl which is unsubstituted or substituted with hydroxy or loweralkoxy, NR$_4$OR$_5$ or ONR$_4$R$_7$, wherein R$_4$, R$_5$ and R$_7$ are independently hydrogen or lower alkyl, R is aryl lower alkyl, which aryl group may be unsubstituted or substituted with an electron withdrawing group and R$_1$ is lower alkyl. In this embodiment it is most preferred that aryl is phenyl, which is unsubstituted or substituted with halo.

It is preferred that R$_2$ is hydrogen and R$_3$ is hydrogen, an alkyl group which is unsubstituted or substituted by at least an electron donating or electron withdrawing group or ZY. In this preferred embodiment, it is more preferred that R$_3$ is hydrogen, an alkyl group such as methyl, which is unsubstituted or substituted by an electron donating group, or NR$_4$OR$_5$ or ONR$_4$R$_7$, wherein R$_4$, R$_5$ and R$_7$ are independently hydrogen or lower alkyl. It is preferred that the electron donating group is lower alkoxy, and especially methoxy or ethoxy.

It is preferred that R$_2$ and R$_3$ are independently hydrogen, lower alkyl, or ZY;

Z is O, NR$_4$ or PR$_4$;

Y is hydrogen or lower alkyl or

ZY is NR$_4$R$_5$R$_7$, NR$_4$OR$_5$, ONR$_4$R$_7$,

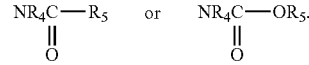

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred R$_1$ is lower alkyl, especially methyl.

It is more preferred that R is aryl lower alkyl and R$_1$ is lower alkyl.

Further preferred compounds are compounds of Formula (Ib) wherein n is 1; R$_2$ is hydrogen; R$_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and R$_1$ is lower alkyl. In this embodiment, it is more preferred that R$_3$ is hydrogen, a lower alkyl group, especially methyl, which may be substituted by electron donating group, such as lower alkoxy, (e.g., methoxy, ethoxy and the like), NR$_4$OR or ONR$_4$R$_7$ wherein these groups are defined hereinabove.

The most preferred compounds utilized are those of the Formula (IIb):

Formula (IIb)

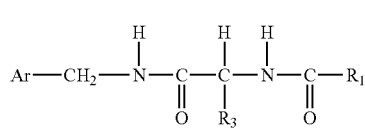

wherein

Ar is aryl, especially phenyl, which is unsubstituted or substituted with at least one electron donating group or electron withdrawing group, especially halo, $R_1$ is lower alkyl, especially containing 1-3 carbon atoms; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, $R_5$ is hydrogen or alkyl containing 1-3 carbon atoms, and $R_7$ is hydrogen or alkyl containing 1-3 carbon atoms.

The most preferred $R_1$ is $CH_3$. The most preferred $R_3$ is $CH_2$-Q, wherein Q is methoxy.

The most preferred aryl is phenyl. The most preferred halo is fluoro.

The most preferred compounds include:
(R)-2-acetamido-N-benzyl-3-methoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

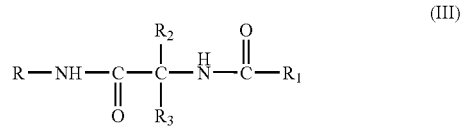

(III)

wherein R, $R_1$, $R_2$, $R_3$, $R_4$, $R_5$, $R_6$, $R'_6$, $R_7$, $R_8$, $R_{50}$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of the utilized compounds is described in U.S. Pat. Nos. 5,378,729 and 5,773,475, the contents of both of which are incorporated by reference.

The compounds utilized in the present invention are useful as such as depicted in the Formulae (Ib) or/and (IIb) or can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds of the present invention are administered in amounts ranging from about 1 mg to about 100 mg per kilogram of body weight per day, more preferably in amounts ranging from about 1 mg to about 10 mg per kilogram of body weight per day. This dosage regimen may be adjusted by the physician to provide the optimum therapeutic response. Patients in need thereof may be treated with doses of the compound of the present invention of at least 50 mg/day, preferably of at least 200 mg/day, more preferably of at least 300 mg/day and most preferably of at least 400 mg/day. Generally, a patient in need thereof may be treated with doses at a maximum of 6 g/day, more preferably a maximum of 1 g/day and most preferably a maximum of 600 mg/day. In some cases, however, higher or lower doses may be needed.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds of the present invention may be administered which results in a plasma concentration of 0.1 to 15 pg/ml (trough) and 5 to 18.5 pg/ml (peak), calculated as an average over a plurality of treated subjects.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal including a human being in need thereof comprises administering a compound of the present invention in combination with administering a further active agent for the prevention, alleviation or/and treatment of a viral infection, such as retroviral infection, HIV infection including AIDS, of cancer such as breast cancer, prostate cancer, lung cancer, bone cancer, metastatic disease, or/and of tumor progression by infiltration in or pressure on bone, viscera, soft tissue or nerves. The compound of the present invention and the further active agent may be administered together, i.e. in a single dose form, or may be administered separately, i.e. in a separate dose form. Thus, the pharmaceutical composition of the present invention may comprise a compound of the present invention as defined above and may further comprise a further active agent for the prevention, alleviation or/and treatment of a viral infection such as retroviral infection, HIV infection including AIDS, of cancer such as breast cancer, prostate cancer, lung cancer, bone cancer, metastatic disease or/and of tumor progression by infiltration in or pressure on bone, viscera, soft tissue or nerves. The pharmaceutical composition may comprise a single dose form or may comprise a separate dose form comprising a first composition comprising a compound of the present invention as defined above and a second composition comprising the further active agent.

The compounds of the present invention may be used for the preparation of a pharmaceutical composition as described above.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (IIb).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition, to curing or alleviating the patient's disease or condition.

The compounds of the present invention are administered to a patient suffering from the aforementioned type of disorder in an effective amount. These amounts are equivalent to the therapeutically effective amounts described hereinabove.

The following example shows the properties of SPM 927 in reducing mechanical and thermal hyperalgesia as well as mechanical and thermal allodynia in a tumor-induced bone cancer pain model, in a chemotherapy-induced and a nucleoside analogue-induced neuropathic pain model.

The used substance was SPM 927 which is the synonym for Harkoseride. The standard chemical nomenclature is (R)-2-acetamide-N-benzyl-3-methoxypropionamide.

FIGURE LEGEND

FIG. 1 describes testing of mechanical allodynia in a bone cancer pain model (rats). Bone cancer rats were treated with increasing concentrations of SPM 927 (10 mg, 20 mg and 40 mg) and compared with morphine treated bone cancer rats, bone cancer rats without treatment (cells only) and control rats.

Figure 2:
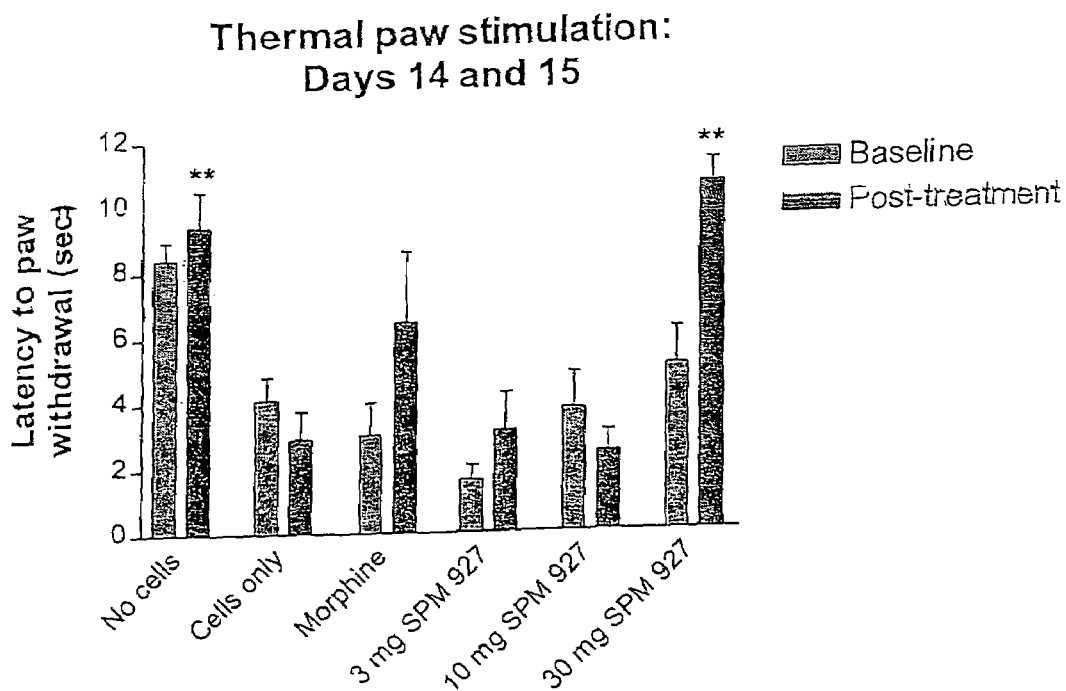

FIG. 2 describes testing of thermal paw stimulation at days 14 and 15 in a bone cancer pain model (rats). Bone cancer rats were treated with increasing concentrations of SPM 927 (3 mg, 10 mg and 30 mg) and compared with morphine treated bone cancer rats, bone cancer rats without treatment (cells only) and control rats.

Figure 3:
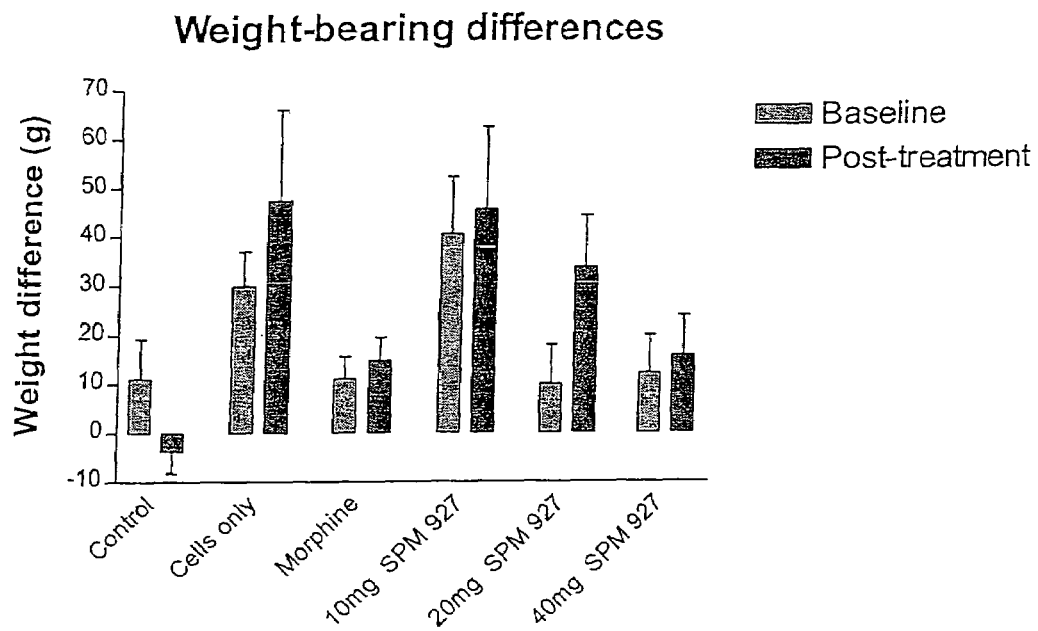
Figure 3:
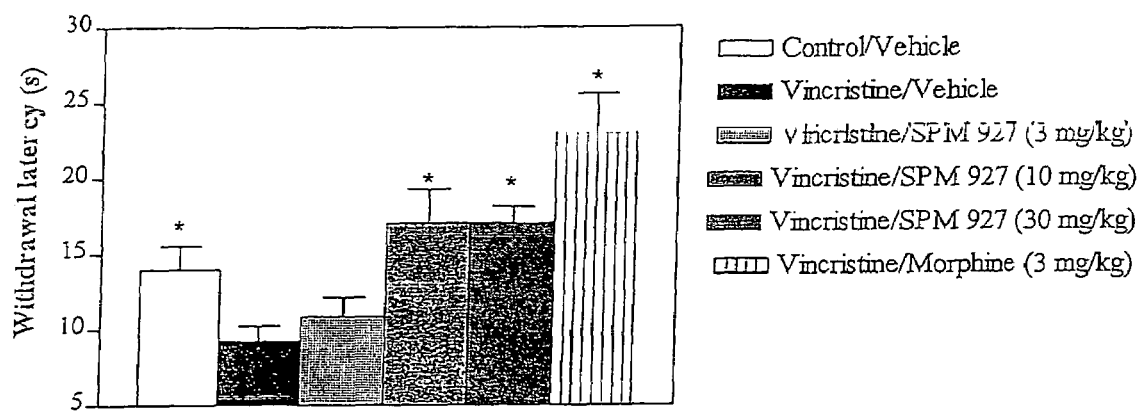

FIG. 3 describes testing of weight bearing differences in a bone cancer pain model (rats). Bone cancer rats were treated with increasing concentrations of SPM 927 (10 mg, 20 mg and 40 mg) and compared with morphine treated bone cancer rats, bone cancer rats without treatment (cells only) and control rats.

FIG. 4 describes the effect of increasing concentrations of SPM 927 (3 mg/kg, 10 mg/kg and 30 mg/kg) on thermal allodynia of cold bath test in a chemotherapy-induced pain model (rats treated with vincristine), compared with morphine (3 mg/kg).

FIG. 5 describes the effect of increasing concentrations of SPM 927 (3 mg/kg, 10 mg/kg and 30 mg/kg) on thermal allodynia of hot plate test at 38° C. in a chemotherapy-induced pain model (rats treated with vincristine), compared with morphine (3 mg/kg).

FIG. 6 describes the effect of increasing concentrations of SPM 927 (3 mg/kg, 10 mg/kg and 30 mg/kg) on thermal hyperalgesia of hot plate test at 52° C. in a chemotherapy-induced pain model (rats treated with vincristine), compared with morphine (3 mg/kg).

FIG. 7 describes the effect of increasing concentrations of SPM 927 (3 mg/kg, 10 mg/kg and 30 mg/kg) on mechanical hyperalgesia of paw pressure test in a chemotherapy-induced pain model (rats treated with vincristine), compared with morphine (3 mg/kg).

FIG. 8 describes the effect of increasing concentrations of SPM 927 (3 mg/kg, 10 mg/kg and 30 mg/kg) on mechanical allodynia of Frey hair stimulation tests in a chemotherapy-induced pain model (rats treated with vincristine), compared with morphine (3 mg/kg).

FIG. 9 describes the effect of increasing concentrations of i.p.-administered SPM 927 (3 mg/kg, 10 mg/kg and 30 mg/kg) in a thermal allodynia test (cold bath) in a nucleoside-induced pain model (rats treated with ddC), compared with the effect of morphine (3 mg/kg administered s.c.).

FIG. 10 describes the effect of increasing concentrations of i.p.-administered SPM 927 (3 mg/kg, 10 mg/kg and 30 mg/kg) in a mechanical allodynia test (brushing at D20) in a nucleoside-induced pain model (rats treated with ddC), compared with the effect of morphine (3 mg/kg administered s.c.).

FIG. 11 describes the effect of increasing concentrations of i.p.-administered SPM 927 (3 mg/kg, 10 mg/kg and 30 mg/kg) in a mechanical allodynia test (von Frey hair) in a nucleoside-induced pain model (rats treated with ddC), compared with the effect of morphine (3 mg/kg administered s.c.).

FIG. 12 describes the effect of increasing concentrations of i.p.-administered SPM 927 (3 mg/kg, 10 mg/kg and 30 mg/kg) in a thermal hyperalgesia test (hot plate at 52° C.) in a nucleoside-induced pain model (rats treated with ddC), compared with the effect of morphine (3 mg/kg administered s.c.).

FIG. 13 describes the effect of increasing concentrations of i.p.-administered SPM 927 (3 mg/kg, 10 mg/kg and 30 mg/kg) in a mechanical hyperalgesia test (paw pressure) in a nucleoside-induced pain model (rats treated with ddC), compared with the effect of morphine (3 mg/kg administered s.c.).

EXAMPLE

The effect of systemic administration of SPM 927 was examined in rats in a tumor-induced bone cancer pain model, in a chemotherapy-induced and a nucleoside analogue-induced neuropathic pain model. SPM 927 reduced mechanical and thermal hyperalgesia as well as mechanical and thermal allodynia in these models. It was demonstrated that SPM 927 is useful as an analgesic for treating bone cancer pain, chemotherapy- and nucleoside-induced neuropathy and is overall more active than morphine.

Materials and Methods

Bone Cancer Rat Model

Cell Culture

Cells were cultured in medium containing RPMI-1640 (Gibco, 500 ml), 10% heat-inactivated fetal bovine serum (Hyclone), L-glutamine (final concentration 2 mM, from Gibco) and antibiotic solution (final concentration 100 U/ml penicillin and 100 ug/ml streptomycin sulfate, from Gibco). Cells were released from the tissue culture flask by brief exposure to 0.1% trypsin (Gibco) and then prepared for injection as follows: cells were centrifuged for 10 minutes at approximately 1,200 rpm. The resulting pellet was washed twice in Phosphate Buffered Saline (PBS, Mediatech) containing no calcium or magnesium. Final pellet was re-suspended in PBS and cell count taken using a hemocytometer. Cells were diluted to achieve final concentrations for injection and kept on ice until injection was performed.

Surgery

After one week of quarantine, either culture media or $3\times10^4$ syngeneic MRMT-1 rat mammary gland carcinoma cells were injected into the medullary cavity of the proximal tibia of each rat. Procedurally, the animal was first anesthetized with ketamine/xylazine and the right leg area shaved and treated with an iodine solution and cleaned with a 70% ethanol solution. A 1-cm rostral-caudal incision was made in the skin over the top half of the tibia. Blunt-dissection was performed to expose the tibia, ensuring minimal damage to muscles or blood vessels. Using a 23-gauge needle, the tibia was pierced, 1-3 mm below the knee joint. The needle was inserted at an angle to enable it to be pushed down into the intramedullary canal of the bone. Once a pathway to the intramedullary canal was opened, the 23-gauge needle was removed and replaced by a blunt needle attached to a 5 μl Hamilton syringe. A 3 μl volume of culture medium+vehicle or tumor cells+vehicle was injected into the intramedullary cavity. The cancer cells were slowly injected while simultaneously removing the syringe, enabling the cells to fill the space in the cavity. Following the injection, the injection site was closed using bone wax. The wound was then closed using surgical staples. Post-operative care and observation was carried out until the animal recovered consciousness Behavior Measurements Dosing On day 8 or 15, the rats were dosed with a single injection of vehicle, reference compound or test article 20 minutes prior to initiation of testing for mechanical allodynia and approximately 40 minutes prior to initiation of testing for thermal hyperalgesia. Based on the pharmacological activity of SPM 927, the tests needed to be performed no longer than 90 minutes after drug treatment. On day 9, the rats were dosed with reference compound or test article 20 minutes prior to initiation of testing for weight bearing.

Nociceptive Evaluations

On days 7, 8, 14 and 15, pain assessment tests were performed. On day 7, 14, the baseline evaluations were performed. All animals received an i.p. injection of saline approximately 20 minutes prior to baseline testing. On day 8, 15 starting approximately 20 minutes after the test/reference article injection, the animals underwent a series of nociceptive evaluations. The order of testing remained the same for all animals. The animals were first evaluated for mechanical allodynia and then thermal hyperalgesia. The animals underwent testing for weight bearing on day 9 and 15. The animals were first evaluated for baseline weight bearing responses. Following the baseline measurements, rats were injected with the test/reference article and at least 20 minutes later, the animals underwent another weight bearing analysis.

Mechanical Allodynia

A Von Frey test of mechanical allodynia was performed on the affected (right) hind limb of all animals at baseline (day 7) and on day 8. In this test, the rats were placed in a small plexiglas box with a wire mesh floor. After approximately 10 min habituation, a series of thin nylon fibers were applied from below, through the cage floor, and pressed against the plantar surface of the hindpaw. The rats were unrestrained and un-handled during the test. The diameters of the filaments provided a logarithmic scale of force exerted and thus a linear and interval scale of perceived intensity. The fiber with the weakest force was tested first and is below the normal threshold of detection for most rats. Each successively strong fiber was tested, in each case using a force required to just start to bend the monofilament. When the rat lifted its paw in response to the pressure, the filament size was recorded and a weaker filament was used next. The withdrawal threshold was determined according to Chapman's "p-down" method involving the use of successively larger and smaller fibers to focus in on the withdrawal threshold. Significant increase in allodynia was based on the comparison of group mean values.

Test of Thermal Hyperalgesia

The animals underwent testing for thermal hyperalgesia at baseline (day 7, 14) and on day 8, 15. Each rat was placed in an individual plexiglas chamber on an elevated heated glass surface for approximately 10 min to habituate. When the animal was at rest, a fiber-optic heat source was guided beneath the glass and aimed at the animal's right hindpaw. The infrared beam was turned on and when the rat lifted or moved its paw, the beam shut off automatically. A timer in the machine recorded the latency to remove the foot, which was taken to signify the time for the animal to detect pain resulting from the heat. If the rat had not moved within 25 sec, the heat source automatically shut off, ensuring that there was no damage to the paw. Only the affected hindpaw was tested. This process was repeated at least twice for each rat, about 3 min apart. If the latencies were within 2 sec of each other, they were averaged. If the latencies differed by more than 2 sec, the rat was tested until there were 2 latencies within 2 sec and these two numbers were averaged. Group means for latency to withdraw the paw were compared across groups with a lower latency indicating more pain sensitivity.

Weight Bearing

After the animals in groups 4-6 were re-randomized to drug treatment groups, on day 9, 15 all animals underwent weight-bearing testing. Weight bearing of affected hind limbs was assessed as the difference in weight borne by the ipsilateral compared to the contralateral limb. Experimentally, the rats were placed in a plexiglas chamber designed so that each hind paw is resting on a separate transducer pad that records the distribution of the animal's body weight on each paw. Five readings from each paw was acquired and then averaged with results expressed as weight bearing difference (WBD; contralateral reading—ipsilateral reading). Rats were allocated eight (8) animals per group based on body weight on the day following arrival. The mean bodyweights for each group was reviewed to ensure that the mean values and standard deviation satisfy the assumption of homogeneity. Based on the Von Frey testing results on day 8, the animals in groups 4-6 were re-randomized to new treatment groups for the weight-bearing test to prevent any bias from their previous group assignment. Animals in groups 1-3 remained within their designated groups since these were animals that were naive to the SPM 927 treatment.

Vincristine-Induced Pain Model

Animal Treatment

For this study, 86 female Dark Agouti rats (150-200 g) were used (Harlan, Gannat, France). They were group-housed (3 animals per cage) and maintained in a room with controlled temperature (21-22° C.) and a reversed light-dark cycle (12 h/12 h) with food and water available ad libitum. All experiments were carried out in accordance with institutional guidelines. Vincristine intoxication was achieved by daily injection of vincristine (0.15 mg/kg/d, i.p.) from day 1 to 5, from day 8 to 12 and days 15 to 16. On day 17, animals were submitted to the behavioral test and received pharmacological treatment. Vincristine-intoxicated rats were randomly distributed in 5 experimental groups (11 rats per group): 1. vincristine/vehicle, i.p.; 2. vincristine/SPM 927 (3 mg/kg), i.p.; 3. vincristine/SPM 927 (10 mg/kg), i.p; 4. vincristine/SPM 927 (30 mg/kg), i.p.; 5. vincristine/morphine (3 mg/kg), s.c. SPM 927 and morphine were respectively injected 30 and 45 min prior to the implementation of behavioral tests.

Cold Bath Test (Thermal Allodynia)

Animals were placed on ice platform submerged approximately 1 cm below the surface of cold water (4° C.), such that the hairy and glabrous skin of the animal feet was in contact with the cold water. The latency before the first reaction (licking, moving the paws, little leaps) was recorded with a cut off time of 30 s.

Hot Plate Test (Thermal Allodynia/Hyperalgesia)

Animals were placed into a glass cylinder on a hot plate (Bioblock, France) adjusted to 38° C. or 52° C. The latency of the first reaction (licking, moving the paws, little leaps or a jump to escape the heat) was recorded with a cut off time of 30 s.

Von Frey Hair Stimulation Test (Mechanical Allodynia)

Rats were placed on a metallic grid floor. The nociceptive testing was done by inserting the von Frey filament (Bioseb, France) through the grid floor and applying it to the plantar surface of the hind paw. A trial consisted of several applications of the different von Frey filaments (at a frequency of 1-1.5 s). The von Frey filaments were applied from filament 10 g to 100 g. The mechanical allodynia threshold was recorded as soon as the animal removed its hind paw the test was stopped and the filament number was recorded.

Paw Pressure Test (Mechanical Hyperalgesia)

The nociceptive flexion reflex was quantified using the Randall-Selitto paw pressure device (Bioseb, France), which applies a linearly increasing mechanical force to the dorsum of the rat's hind paw. The mechanical nociceptive threshold was defined as the force in grams at which the rat withdrew its paw. The cut off pressure was set to 250 g.

Data Analysis

ANOVA followed by post-hoc analysis (Dunnett's test) was used to compare groups of behavioral data in each individual time points.

Nucleoside-Induced Pain

Animals, ddC Intoxication and Experimental Groups

For this study, 50 male Sprague Dawley (~220 g) rats were used (Janvier, Le Genest-St-lsle, France). Rats were group-housed (3 animals per cage) and maintained in a room with controlled temperature (21-22° C.) and a reversed light-dark cycle (12 h/12 h) with food and water available ad libitum. All experiments were carried out in accordance with institutional guidelines. Intoxication was achieved by a single injection of ddC (50 mg/kg, I.V. in tail vein). On day 10 and day 20, animals were submitted to the behavioral test and received pharmacological treatment. ddC-intoxicated rats were randomly distributed in 5 experimental groups (10 rats per group): 1. control/vehicle,ip, 2. ddC/vehicle, i.p.; 3. ddC/SPM 927 (3 mg/kg), i.p.; 3. ddC/SPM 927 (10 mg/kg), i.p; 4. ddC/SPM 927 (30 mg/kg), i.p.; 5. ddC/morphine (3 mg/kg), s.c. SPM 927 and morphine were respectively injected 30 and 45 min prior to the implementation of behavioral tests.

Brushing Test Day 20

The hair on the legs, flanks, and lower back was sequentially brushed with a cotton-tipped applicator using an oscillating motion (rate of 1-2/s; 30 sec). Brushing was done with no more force than required to move the applicator through the hair such that only the pelage is disturbed. Vocalization and moderate effects to avoid the brushing were counted.

Results

Bone Cancer Rat Model

Mechanical Allodynia

FIG. 1 depicts group responses to the Von Frey filaments following baseline testing and following drug treatment. The statistical analysis performed using an overall 2-way ANOVA was significantly different for treatment group (p<0.01), but not for baseline vs. treatment effects. One-way ANOVA tests comparing the "cells only" group following "treatment" with each of the treatment groups revealed significant differences in the level of mechanical allodynia for the morphine group (p<0.01), and the 20 and 40 mg/kg SPM 927 group (p<0.05). The 5 mg/kg morphine treatment completely reversed the allodynia that was revealed at the time of baseline testing. In addition, a highly significant difference was demonstrated between the "post-treatment" data for the healthy and tumor-injected "cells only" group (p<0.01). Statistical differences also exist between the baseline values and post-dose values for the "cells only" group and the morphine group (p<0.01).

Thermal Hyperalgesia

The data for thermal paw testing (FIG. 2) on Days 14 and 15 show that the baseline latencies to remove their paws for all tumor-injected groups were. This was confirmed to be highly significant with a two-way ANOVA, in which the drug effect was p<0.0001 and the effect of treatment was significant at p<0.05. The baseline or pre-treatment data were significantly different for the "no cells" vs. "cells only" groups (Dunnett's post-hoc test; p<0.001) with the other groups showing no differences from one another. In addition, the post-treatment groups were different for "no cells" vs. "cells only" (Dunnett's; p<0.001) and "cells only" vs. SPM 927 30 mg/kg dose (Dunnett's; p<0.001). The morphine control group did not show statistical significance although there was a trend indicating that morphine increased the latency to paw removal.

Mechnical Hyperalgesia

The graph (FIG. 3) shows an overall 2-way ANOVA showed significant group differences, 0<0.001. Since weight-bearing differences were defined as the weight borne by the contralateral leg minus the weight borne by the ipsilateral (tumor-injected) leg, a higher number would indicate more weight on the non-affected paw with 0 meaning equal weight distribution on both paws. The baseline data collected showed a positive number, revealing that these animals are all placing more weight on their non-affected paws. In comparison to the "cells only" group, the morphine group and the 40 mg/kg SPM 927 groups showed a significant reduction (p<0.05) in the amount of weight placed on their contralateral paws following treatment, as compared to the "cells only" group.

Vincristine-Induced Pain

Cold Bath Test

As shown in FIG. 4, a significant statistical difference was seen between the 6 groups (p<0.05, Anova test). Vincristine-animals treated with the vehicle displayed very short threshold latency in the cold bath test (about 9 s) in contrast with control animals showing a time score about 14 s. Treatment of vincristine-animals with SPM 927 induced a significant increase (p<0.05, Dunnett's test) in the threshold latency, which became indeed comparable to that of control animals, especially for the treatment doses of 10 and 30 mg/kg. At 3 mg/kg however, the threshold latency was slightly greater than that of vincristine-animals, although statistical difference was not reached. Morphine treatment extended the threshold latency of vincristine-animals to a level far above that obtained from control rats.

Hot Plate Test at 38° C.

FIG. 5 shows that the threshold latency of vincristine-animals in the hot plate (38° C.) test was significantly shorter than that of control animals (p<0.05, Dunnett's test). Treatment of vincristine-rats with SPM 927 at 3, 10 and 30 mg/kg induced a significant (p<0.05, Dunnett's test) increase in the threshold latency. With the treatment doses of 10 and 30 mg/kg, the performance of STZ-rats became comparable with that of control animals. Similarly to SPM 927 at 10 and 30 mg/kg, morphine at 3 mg/kg extended the threshold latency of STZ-animals to a level comparable with that of control rats.

Hot Plate Test at 52 C.

As illustrated in FIG. 6, the paw withdrawal latency of vincristine-rats was significantly shorter than that of control animals (p<0.05, Dunnett's test). Treatment of vincristine-rats with SPM 927 induced a significant increase (p<0.05, Dunnett's test) in paw withdrawal latency in as compared with vehicle-treated animals. The effect obtained with the doses of 3 and 10, 30 mg/kg was comparable with that of control.

Paw Pressure Test

Using the analgesy-meter of Randall & Selitto, vincristine-animals demonstrated a marked decrease in the paw withdrawal latency as compared with the performance of control animals (FIG. 7). Treatment of vincristine-rats with SPM 927 at the doses of 10 and 30 mg/kg, but not at 3 mg/kg, induced a significant increase (p<0.05, Dunnett's test) in paw withdrawal latency of vincristine-rats. In this test, morphine treatment did not modify the performance of vincristine-rats (p>0.05, Dunnett's test).

Von Frey Filament Test

In this test (FIG. 8), the paw withdrawal latency of vincristine-rats was significantly reduced (about 20 g) as compared with that of control rats (about 60 g). Treatment with SPM 927 extended the paw withdrawal latency of vincristine rats. The difference with the vehicle-treated group reached the significance level with the treatment doses of 10 and 30 mg/kg (p<0.05, Dunnett's test). Morphine treatment restored the performance of vincristine-rats to a level comparable with that of control group.

Nucleoside-Induced Pain Rat Model

Thermal Allodynia

As shown in FIG. 9, a significant statistical difference was seen between the 6 groups (p<0.05, Anova test). ddC-animals treated with the vehicle displayed very short threshold latency in the cold bath test (about 11 s) in contrast with control animals showing a time score about 20 s. Treatment of ddC-animals with SPM 927 induced a significant increase (p<0.05, Dunnett's test) in the threshold latency, which became indeed comparable to that of control animals for the 3 test doses, 3, 10 and 30 mg/kg. Morphine treatment extended the threshold latency of ddC-animals to a level comparable to that obtained from control rats.

Brushing Test at Day 20

FIG. 10 shows the results of brushing test performed on D 20. The animals treated with SPM 927 (at 3, 10 and 30 mg/kg) displayed a significant decrease in the total number of cries (p<0.05, Dunnett's test). Here again, morphine at 3 mg/kg was able to significantly decrease the total number of cries in the ddC-animals.

Von Frey Filament Test at D10

In this test (FIG. 11), the paw withdrawal latency of ddC-rats was significantly reduced (about 50 g) as compared with that of control rats (about 85 g). Treatment with SPM 927 extended the paw withdrawal latency of ddC rats. The difference with the vehicle-treated group reached the significance level with the treatment doses of 3, 10 and 30 mg/kg (p<0.05, Dunnett's test) to a level comparable to control group. Morphine treatment at 3 mg/kg restored the performance of ddC-rats to a level similar to control group.

Hot Plate Test at 52° C. at D20

As illustrated in FIG. 12, the paw withdrawal latency of ddC-rats was significantly shorter than that of control animals (p<0.05, Dunnett's test). Treatment of ddC-rats with SPM 927 only at the dose of 30 mg/kg, induced a significant increase (p<0.05, Dunnett's test) in paw withdrawal latency in as compared with vehicle-treated animals. The effect obtained with the doses of 3 and 10 mg/kg was comparable with untreated vehicle group. Following morphine treatment, the performance of ddC-rats became similar with that of control animals.

Paw Pressure Test at D10

Using the analgesy-meter of Randall & Selitto, ddC-animals demonstrated a marked decrease in the paw withdrawal latency as compared with the performance of control animals (FIG. 13). Treatment of ddC-rats with SPM 927 at all the 3 doses of 3, 10 and 30 mg/kg induced a significant increase ($p<0.05$, Dunnett's test) in paw withdrawal latency of ddC-rats. Again morphine treatment increased the performance of ddC-rats ($p<0.05$, Dunnett's test).

CONCLUSION

Systemic SPM 927 produced a dose-dependent anti-allodynic and anti-hyperalgeisc effect in a rat model of bone cancer pain, chemotherapy- and nucleoside-induced pain following single dose administration. Thus, SPM 927 and related compounds as disclosed in formulae (Ib) or/and (IIb) are useful for the treatment of pain during cancer, e.g. bone cancer pain, after treatment with chemotherapy and nucleosides in humans.

REFERENCES

Medhurst, S. J., Walker, K., Bowes, M., Kidd, B. L., Glatt, M., Muller, M., Hattenberger, M., Vaxelaire, J., O'Reilly, T. O., Wotherspoon, G., Winter, J., Green, J., and Urban, L. A rat model of bone cancer pain. Pain, 96: 129-140, 2002.

Casey E B, Jellife A M, Le Quesne P M, Millett Y L. Vincristine neuropathy. Clinical and electrophysiological observations. Brain 1973; 96: 69-86.

Weiss H D, Walker M D, Wiernik P H. Neurotoxicity of commonly used antineoplastic agents (second of two parts). N Engl J Med. 1974 ; 291(3): 127-33.

Quasthoff S, Hartung H P Chemotherapy-induced peripheral neuropathy J Neurol (2002) 249: 9-17.

Kimberly D. Tanner, David B. Reichling, and Jon D. Levine. Nociceptor Hyper-Responsiveness during Vincristine-Induced Painful Peripheral Neuropathy in the Rat. J Neurosc (1998) 18(16):6480-6491.

Kaplan R S, Wiernik P H Neurotoxicity of antineoplastic drugs. (1982) Semin Oncol 9:103-130.

Owellen R J, Hartke C A, Dickerson R M, Hains F O (1976) Inhibition of tubulin-microtubule polymerization by drugs of the vinca alkaloid class. Cancer Res 36:1499-1502.

Sandier S G, Tobin W, Henderson E S (1969) Vincristine-induced neuropathy. A clinical study of fifty leukemic patients. Neurology 19:367-374.

Holland J F, Scharlau C, Gailani S, Krant M J, Olson K B, Shnider B I, Lynch J J, Owens A, Carbone P P, Colsky J, Grob S P, Hall T C (1973) Vincristine treatment of advanced cancer: cooperative study of 392 cases. Cancer Res 33:1258-1264.

McCarthy G M, Skillings J R (1992) Jaw and other orofacial pain in patients receiving vincristine for the treatment of cancer. Oral Surg Oral Med Oral Pathol 74:299-304.

Aley K O, Levine J D. Different mechanisms mediate development and expression of tolerance and dependence for peripheral mu-opioid antinociception in rat. J Neurosci 1997; 17:8018-23.

Aley K O, Levine J D. Role of protein kinase A in the maintenance of inflammatory pain. J Neurosci 1999; 19:2181-6.

Aley K O, Levine J D. Different peripheral mechanisms mediate enhanced nociception in metabolic/toxic and traumatic painful peripheral neuropathies in the rat. Neuroscience 2002; 111 :389-97.

Aley K O, McCarter G, Levine J D. Nitric oxide signaling in pain and nociceptor sensitization in the rat. J Neurosci 1998; 18:7008

Kaplan R S, Wiernik P H Neurotoxicity of antineoplastic drugs. (1982) Semin Oncol 9:103-130.

Cohen J. Therapies. Confronting the limits of success. Science 2002; 296: 2320-4.

Dalakas M C. Peripheral neuropathy and antiretroviral drugs. J Peripher Nerv Syst 2001; 6:14-20.

Dalakas M C, Semino-Mora C, Leon-Monzon M. Mitochondrial alterations with mitochondrial DNA depletion in the nerves of AIDS patients with peripheral neuropathy induced by 2030-dideoxycytidine (ddC). Lab Invest 2001; 81 :1537-44.

Dina O A, Barletta J, Chen X, Mutero A, Martin A, Messing R O, Levine J D. Key role for the epsilon isoform of protein kinase C in painful alcoholic neuropathy in the rat. J Neurosci 2000; 20:8614-9.

Dubinsky R M, Yarchoan R, Dalakas M, Broder S. Reversible axonal neuropathy from the treatment of AIDS and related disorders with 20,30-dideoxycytidine (ddC). Muscle Nerve 1989; 12:856-60.

Josepha E K, Chena X, Khasara S G, Levinea J D. Novel mechanism of enhanced nociception in a model of AIDS therapy-induced painful peripheral neuropathy in the rat. Pain 107 (2004) 147-158.

Williams D, Geraci A, Simpson D M. AIDS and AIDS-treatment neuropathies. Curr Neurol Neurosci Rep 2001; 1:533-8.

Yatvin M B, Li W, Meredith M J, Shenoy M A. Improved uptake and retention of lipophilic prodrug to improve treatment of HIV. Adv Drug Deliv Rev 1999; 39:165-8

The invention claimed is:

1. A method for alleviating and/or treating bone cancer pain and/or chemotherapy-induced pain in a subject, comprising administering to the subject (R)-2-acetamido-N-benzyl-3-methoxypropionamide or a pharmaceutically acceptable salt thereof.

2. The method of claim 1, wherein the chemotherapy-induced pain is chemotherapy-induced neuropathic pain and/or vinca alkaloid-induced pain.

3. The method of claim 1, wherein the (R)-2-acetamido-N-benzyl-3-methoxypropionamide or salt thereof is substantially enantiopure.

4. The method of claim 1, wherein the (R)-2-acetamido-N-benzyl-3-methoxypropionamide or salt thereof is administered at a dose of 100 mg/day to 6 g/day.

5. The method of claim 1, wherein the (R)-2-acetamido-N-benzyl-3-methoxypropionamide or salt thereof is administered at a dose of 200 mg/day to 1 g/day.

6. The method of claim 1, wherein the (R)-2-acetamido-N-benzyl-3-methoxypropionamide or salt thereof is administered at increasing daily doses until a predetermined daily dose is reached which is maintained during further treatment.

7. The method of claim 1, wherein the (R)-2-acetamido-N-benzyl-3-methoxypropionamide or salt thereof is administered in no more than three doses per day.

8. The method of claim 1, wherein the (R)-2-acetamido-N-benzyl-3-methoxypropionamide or salt thereof is administered in a pharmaceutical composition resulting in a plasma concentration of 0.1 to 15 µg/ml (trough) and 5 to 18.5 µg/ml (peak), calculated as an average over a plurality of treated subjects.

9. The method of claim 1, wherein the (R)-2-acetamido-N-benzyl-3-methoxypropionamide or salt thereof is administered orally or intravenously.

10. The method of claim 1, wherein the subject is a mammal.

11. The method of claim 10, wherein the subject is human.

12. The method of claim 2, wherein the vinca alkaloid-induced pain is vincristine-induced pain.

* * * * *

UNITED STATES PATENT AND TRADEMARK OFFICE
CERTIFICATE OF CORRECTION

| | | |
|---|---|---|
| PATENT NO. | : 7,687,553 B2 | Page 1 of 1 |
| APPLICATION NO. | : 11/211476 | |
| DATED | : March 30, 2010 | |
| INVENTOR(S) | : Bettina Beyreuther | |

It is certified that error appears in the above-identified patent and that said Letters Patent is hereby corrected as shown below:

Column 1, line 54, "$NR_4OR$" should be changed to --$NR_4OR_5$--; line 55, "$PR_4{}_OR_5$" should be changed to --$PR_4OR_5$--.

Column 5, line 40, "$N'R_5R_6R_7$" should be changed to --$N^+R_5R_6R_7$--.

Column 9, line 27, "O" should be changed to --0--.

Column 10, line 2, "$NR_4{}_OR_5$" should be changed to --$NR_4OR_5$--; line 52, "$NR_4OR$" should be changed to --$NR_4OR_5$--.

Column 13, line 23, "15 pg/ml" should be changed to --15 µg/ml--; line 24, "18.5 pg/ml" should be changed to --18.5 µg/ml--.

Column 18, line 48, "p-down" should be changed to --up-down--.

Signed and Sealed this

Thirteenth Day of July, 2010

David J. Kappos
*Director of the United States Patent and Trademark Office*